(12) United States Patent
Petitt

(10) Patent No.: US 9,572,708 B2
(45) Date of Patent: Feb. 21, 2017

(54) THERMAL WRAP WITH INTEGRAL THERMAL MEDIA ARRAY AND SUPPORT FOR TRANSCUTANEOUS ELECTRICAL NERVE STIMULATION

(71) Applicant: Steven Petitt, Atlantic Beach, FL (US)

(72) Inventor: Steven Petitt, Atlantic Beach, FL (US)

( * ) Notice: Subject to any disclaimer, the term of this patent is extended or adjusted under 35 U.S.C. 154(b) by 0 days.

(21) Appl. No.: 15/006,676

(22) Filed: Jan. 26, 2016

(65) Prior Publication Data

US 2016/0213509 A1 Jul. 28, 2016

Related U.S. Application Data

(60) Provisional application No. 62/107,690, filed on Jan. 26, 2015.

(51) Int. Cl.
*A61N 1/04* (2006.01)
*A61F 7/02* (2006.01)
*A61N 1/36* (2006.01)

(52) U.S. Cl.
CPC .............. *A61F 7/02* (2013.01); *A61N 1/0456* (2013.01); *A61N 1/0492* (2013.01); *A61N 1/36014* (2013.01); *A61F 2007/0228* (2013.01); *A61F 2007/0242* (2013.01); *A61F 2007/0244* (2013.01); *A61F 2007/0269* (2013.01)

(58) Field of Classification Search
CPC ... A61N 1/0412; A61N 1/0452; A61N 1/0456
See application file for complete search history.

(56) References Cited

U.S. PATENT DOCUMENTS

| | | | | |
|---|---|---|---|---|
| 5,823,989 | A * | 10/1998 | Ostrow | A61N 1/044 604/20 |
| 7,758,527 | B2 * | 7/2010 | Gilmour | A61F 5/0106 602/23 |
| 2005/0043655 | A1 * | 2/2005 | Schenck | A61H 23/02 601/15 |
| 2010/0211122 | A1 * | 8/2010 | Hensley | A61F 7/02 607/3 |

* cited by examiner

*Primary Examiner* — Christopher D Koharski
*Assistant Examiner* — Natasha Patel
(74) *Attorney, Agent, or Firm* — Mark Young, PA

(57) ABSTRACT

A wrap has a thermal media laminate containing an array of spaced apart cells of thermal media sandwiched between a plastic film and fabric. Areas in the laminate are provided for attaching electrodes. The laminate is attached to a backing. Apertures in the laminate and backing allow passage of wire leads from the electrodes. Elastic bands with hook fasteners extend from the backing. The hook fasteners releasably attach to loop material of the backing. A TENS unit clips onto one or more of the bands. The leads attach to the TENS unit.

3 Claims, 5 Drawing Sheets

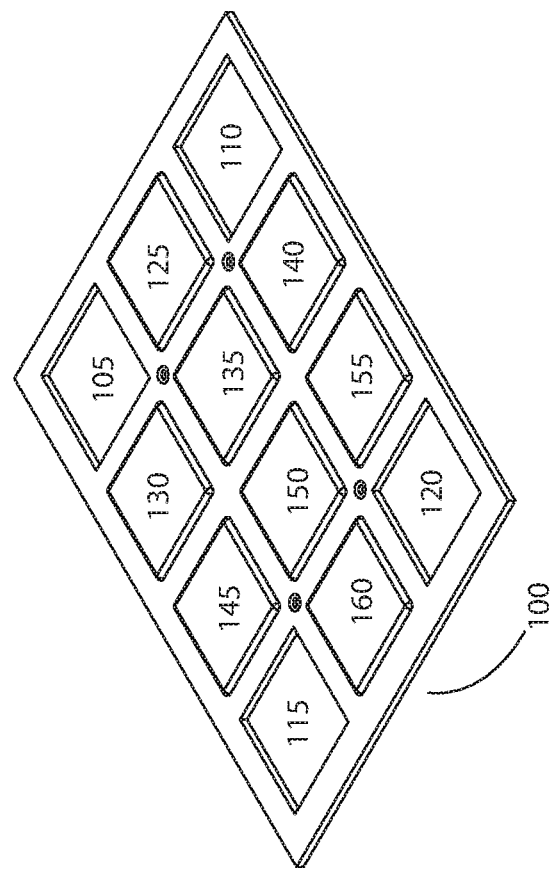
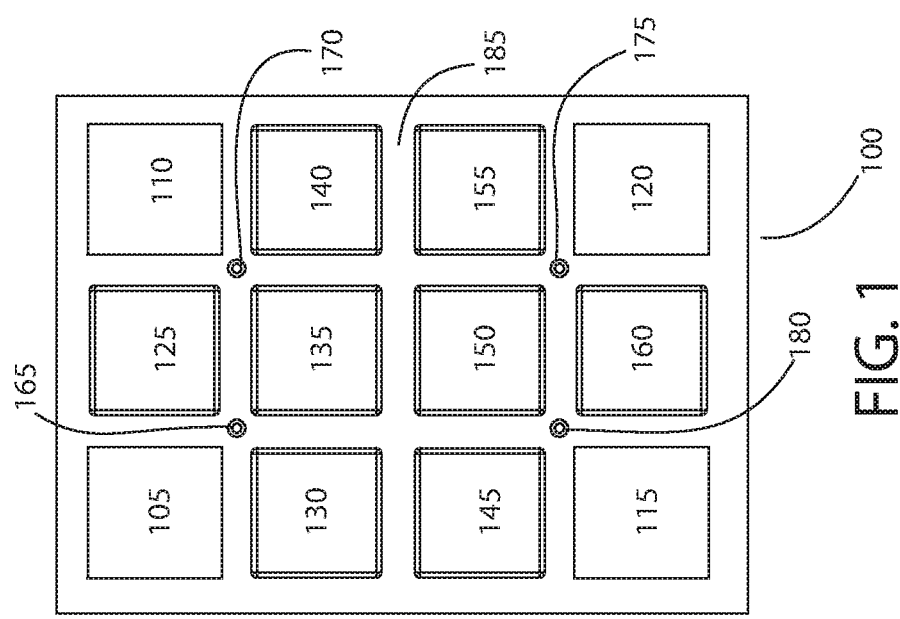

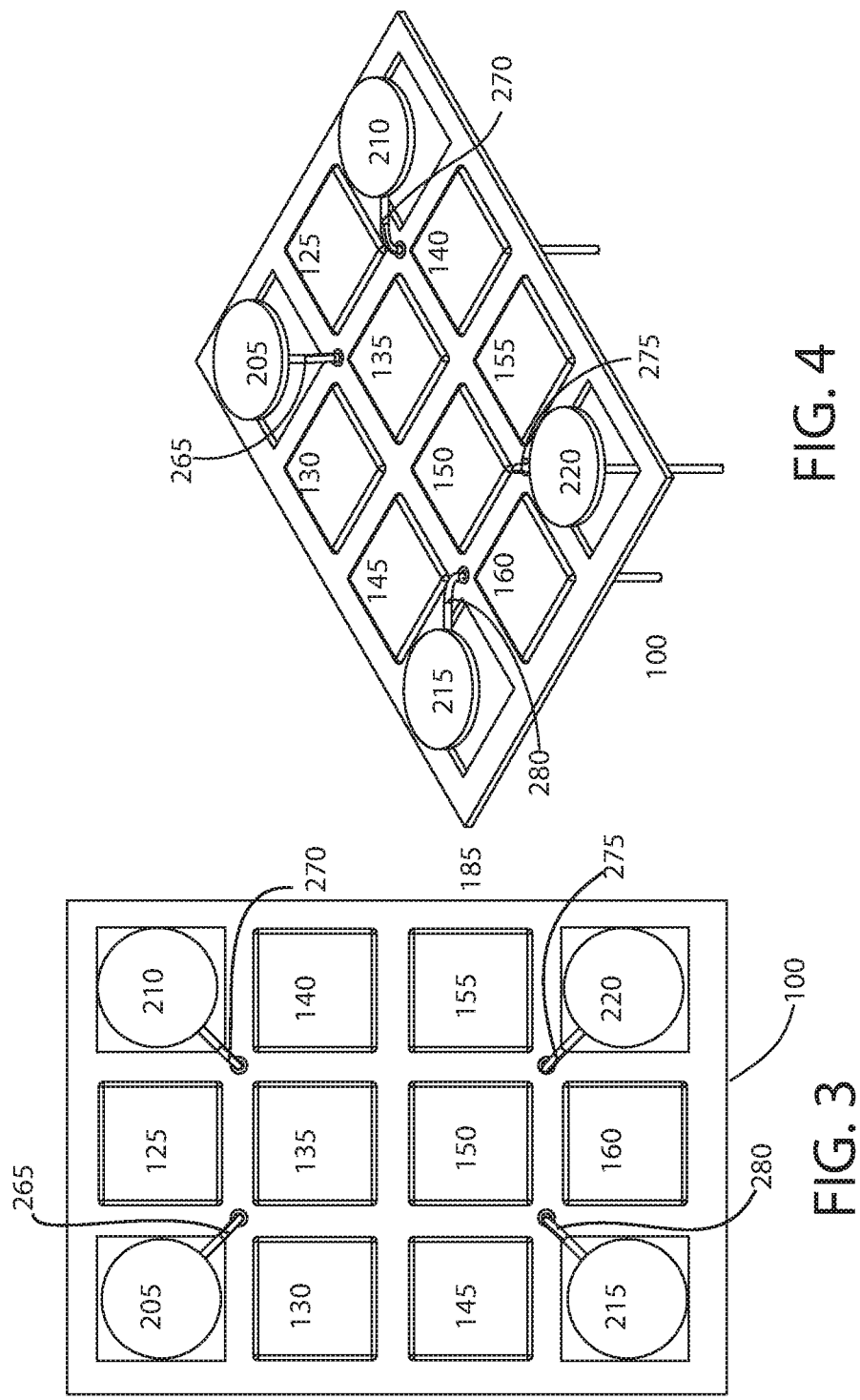

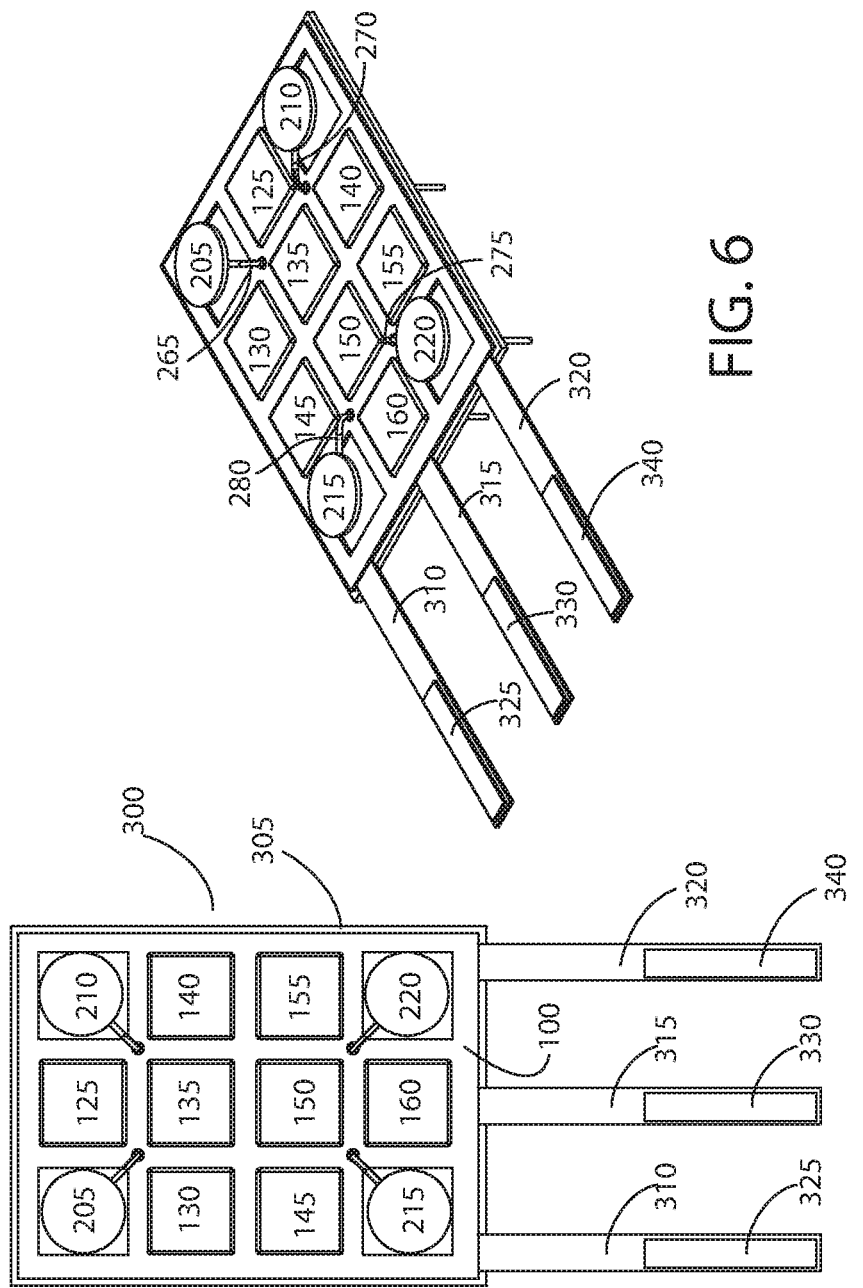

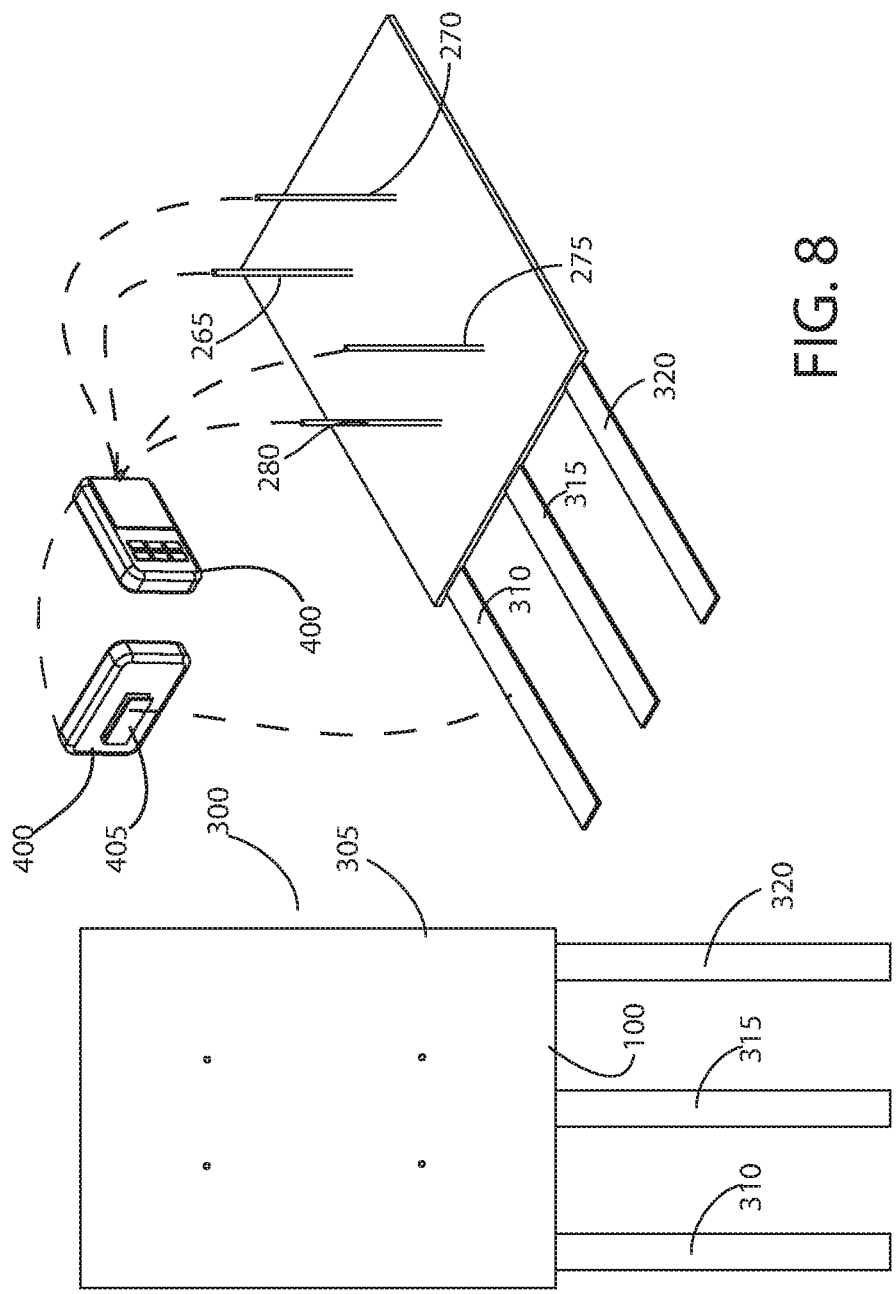

THERMAL WRAP WITH INTEGRAL THERMAL MEDIA ARRAY AND SUPPORT FOR TRANSCUTANEOUS ELECTRICAL NERVE STIMULATION

RELATED APPLICATION

This application is a nonprovisional and claims the benefit of priority of U.S. Provisional Application No. 62/107,690, filed Jan. 26, 2015.

FIELD OF THE INVENTION

This invention relates therapeutic wraps, and, more particularly, to a wrap that contains an integral thermal media array and supports transcutaneous electrical nerve stimulation.

BACKGROUND

Transcutaneous electrical nerve stimulation (TENS) uses electrical stimuli to stimulate nerves for therapeutic purposes. A TENS unit connects to the skin using two or more electrodes. A typical battery-operated TENS unit is able to modulate pulse width, frequency and intensity of the electrical energy supplied through the electrodes. The electrodes usually consist of a conducting gel, which may be adhesive or coated with an adhesive. A cable or lead extends from the TENS unit to each electrode. The electrodes deliver the electrical stimulus.

Heating and cooling are useful for relieving sore aching muscles and post surgical treatment. Cooling and heating wraps typically consist of a garment with pockets that contain a bulky sack containing a liquid or gel cooling or heating substance. When frozen, the sack forms a solid brick-like mass.

As both TENS and thermal therapy may benefit the same parts of the body, it is desirable to have a device that supports both and delivers electrical stimulation with heating or cooling. Unfortunately, units developed heretofore utilize bulky thermal media sacks that tend to interfere with placement and adherence of TENS electrodes. What is needed is a wrap with an integral thermal media that distributes weight and maintains its form throughout the thermal therapy, while allowing attachment of TENS electrodes and a coupled TENS unit.

The invention is directed to overcoming one or more of the problems and solving one or more of the needs as set forth above.

SUMMARY OF THE INVENTION

To solve one or more of the problems set forth above, in an exemplary implementation of the invention, a wrap includes an integral thermal media array and supports transcutaneous electrical nerve stimulation. The wrap has a thermal media laminate containing an array of spaced apart cells of thermal media sandwiched between a plastic film and fabric. The cellular laminate is flexible, foldable and wrappable. Areas in the laminate are provided for attaching electrodes. The laminate is attached to a backing. Apertures in the laminate and backing allow passage of wire leads from the electrodes. Elastic bands with hook fasteners extend from the backing. The hook fasteners releasably attach to loop material of the backing. A TENS unit clips onto one or more of the bands. The leads attach to the TENS unit.

In one embodiment, a wearable nerve-stimulating thermal wrap according to principles of the invention includes a thermal media laminate comprised of a web of plastic film sealed at a plurality of locations to a web of fabric with spaces between the sealed locations comprising cells. Each cell is a pocket surrounded by locations at which the plastic film is sealed to the web of fabric. Each cell contains an absorbent solid state thermal medium. The thermal media laminate further comprises at least one electrode area, each electrode area being devoid of cells and being sized and shaped to receive a transcutaneous electrical nerve stimulation electrode. An insulating backing is attached to the plastic film opposite the web of fabric. A transcutaneous electrical nerve stimulation electrode is attached to at least one electrode area. A wire lead extends from the transcutaneous electrical nerve stimulation electrode. A first aperture is provided in the thermal media laminate at one of the locations at which the plastic film is sealed to the web of fabric adjacent to one of the at least one electrode area. A second aperture is provided in the insulating backing in alignment with the first aperture. The wire lead of the transcutaneous electrical nerve stimulation electrode extends through the first aperture and the second aperture. An attachment band is attached to the thermal media laminate. The attachment band is sized to releasably secure the thermal media laminate to a wearer. A transcutaneous electrical nerve stimulation unit is operably coupled to the wire lead of the transcutaneous electrical nerve stimulation electrode. The at least one electrode area may comprise a fenestration in the thermal media laminate. The absorbent solid state thermal medium may comprise a superabsorbent, multiply-cross-linked polymer.

BRIEF DESCRIPTION OF THE DRAWINGS

The foregoing and other aspects, objects, features and advantages of the invention will become better understood with reference to the following description, appended claims, and accompanying drawings, where:

FIG. 1 is a plan view of an exemplary thermal media laminate for use with a wrap according to principles of the invention; and FIG. 2 is a perspective view of an exemplary thermal media laminate for use with a wrap according to principles of the invention; and FIG. 3 is a plan view of an exemplary thermal media laminate equipped with electrodes for use with a wrap according to principles of the invention; and FIG. 4 is a perspective view of an exemplary thermal media laminate equipped with electrodes for use with a wrap according to principles of the invention; and FIG. 5 is a plan view of an exemplary wrap according to principles of the invention; and FIG. 6 is a perspective view of an exemplary wrap according to principles of the invention; and FIG. 7 is a bottom view of an exemplary wrap according to principles of the invention; and FIG. 8 is a bottom perspective view of an exemplary wrap according to principles of the invention.

Figure 9:
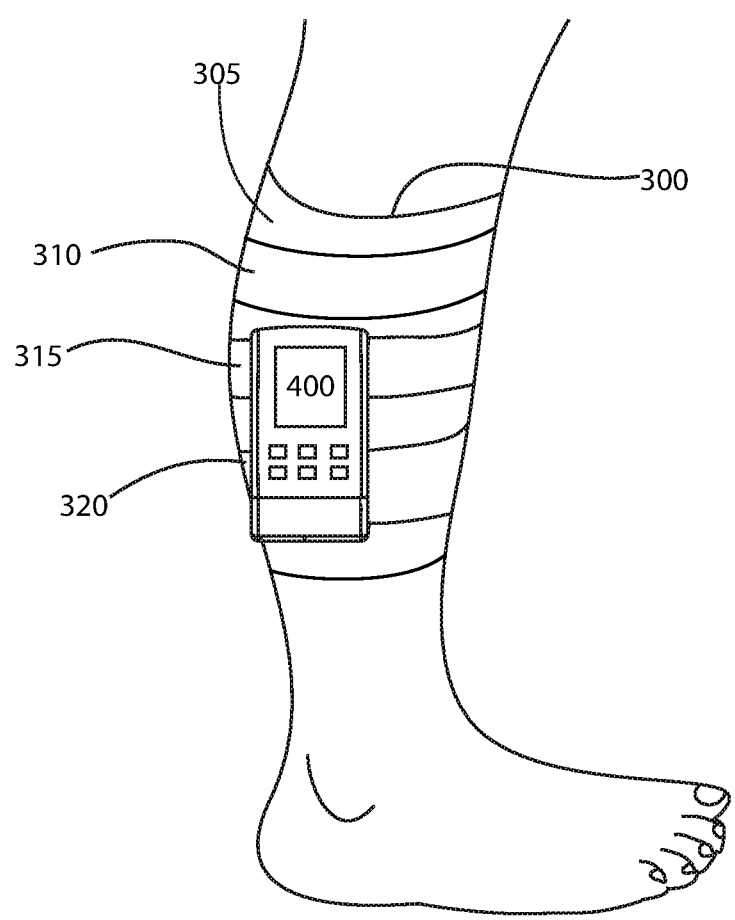
FIG. 9 is a side view of an exemplary wrap, wrapped around a wearer's limb, according to principles of the invention.

Those skilled in the art will appreciate that the figures are not intended to be drawn to any particular scale; nor are the figures intended to illustrate every embodiment of the invention. The invention is not limited to the exemplary embodiments depicted in the figures or the specific components, configurations, shapes, relative sizes, ornamental aspects or proportions as shown in the figures.

DETAILED DESCRIPTION

Referring to FIGS. 1 through 4, various views of an exemplary thermal media laminate 100 for use with a wrap according to principles of the invention is provided. The laminate 100 consists of a web of plastic film (e.g., an impervious plastic sheet such as a polyester film) sealed to a web of non-woven fabric (e.g., a non-woven porous polypropylene) at parallel and perpendicular strips, thus forming a grid of, for example, two inch by two inch (2"×2") cells 125-160 or pockets across the web. The cellular arrangement facilitates bending and wrapping. Sealing may be performed using a tacky, sealant or adhesive layer (e.g., ethylene-methyl-acrylate (EMA)), or using a heat sealing tape, or other suitable sealants for merging plastic and fabric. A small volume of a solid state thermal medium, such as a superabsorbent, multiply-cross-linked polymer is provided within each such cell. The solid thermal medium is adhesively fixed to areas of the plastic film destined to comprise cells 125-160. Each cell resembles a thin pillow when dehydrated and a puffy pillow when hydrated. The sealed strips 185 not only define the peripheries of the laminate 100 and each cell, but also provide substantially flat areas suitable for stitching the laminate 100 to a cover, as discussed below.

The laminate 100 also includes an area ("electrode area") for mounting each of a plurality of electrodes 205-220. Each such electrode area 105-120 may comprise a fenestration (e.g., a cutout or window) or a planar area without any thermal medium. Each electrode area 105-120 is sized and shaped to receive a TENS electrode 205-220, and positioned to locate each electrode 205-220 in a desired position on a wearer's body when the wrap is worn and used. The number and position of electrodes may vary without departing from the scope of the invention. The wrap may be used with and without electrodes, in accordance with the invention.

Passages 165-180 for wire leads 265-280 from the electrodes 205-220 are also provided in the laminate 100. By way of example and not limitation, a passage may be provided in a sealed strip 185 adjacent to an electrode area 105-120. In the figures, grommets define the passages. Wires 265-280 extending from the electrodes 205-220 pass through these grommets and corresponding apertures. As the electrodes 205-220 are replaceable, the passages 165-180 allow withdrawal of the received wires 265-280. Thus, the passages 165-180 are sized and positioned to allow passage of the electrode wires 265-280.

Referring now to FIGS. 5 through 8, the laminate 100 of the wrap 300 is attached to a backing 305 305. The backing 305 provides an insulating and protective cover. It also facilitates attaching the wrap. The backing 305 may comprise neoprene laminated with a nylon low pile soft loop fabric, which is compatible with hook fasteners. The plastic side of the laminate 100 abuts the neoprene backing 305. The loop fabric side of the neoprene, which provides a surface for attachment of hook elements of a hook and loop fastener, faces away from the laminate 100. The fabric side of the laminate 100, which will abut a wearer, faces away from the backing 305. The laminate 100 may be attached to the backing 305 by stitching and/or bonding. In a preferred embodiment, the laminate 100 is stitched to the backing 305, with stitching along the sealed strips 185.

The backing 305 includes a plurality of apertures aligned with the apertures and grommets of the laminate 100. The wire leads 265-280 of the electrodes 205-220 extend through the apertures of the backing 305.

A plurality of elastic bands 310-320 extend from an edge of the backing 305. The side of each band 310-320 facing the laminate 100 includes hook elements 325-350 of a hook and loop fastener. When the wrap 300 is wrapped around a limb, the hook elements 325-340 are attachable to the loop fabric side of the neoprene backing 305. Elasticity of the bands 310-320 allows considerable adaptation for attachment to various body parts. The plurality of elastic bands 310-320 do not have to extend from the same edge. One or more bands 310-320 may extend from an edge that is orthogonal to or opposite from an edge from which one or more other bands 310-320 extend.

A TENS unit 400 attaches to one or more bands 310-320. The back of most commercially available TENS units is equipped with a clip 405 for attachment to a belt. The bands 310-320 are sufficiently wide and supportive to securely hold the TENS unit. The wire leads 265-280 of the electrodes 205-220 extend through the apertures in the laminate 100 and backing 305 and connect to the TENS unit 400.

To prepare the wrap 300 for use, the electrodes are removed from the wrap. Then the laminate 100 is hydrated using water. Tap water at room temperature works well. The polymer media contained in the laminate 100 absorbs the water and expands. After a few minutes of hydration, the hydrated wrap 300 is frozen in a freezer or heated in a microwave. Then the electrodes are installed, with leads extending through the laminate 100 and backing 305 to the TENS unit 400. Then the wrap 300 is wrapped around a user's limb or other body part to be treated. The TENS unit 400 is clipped to one or more bands 310-320, as conceptually illustrated in FIG. 9. Then the TENS unit 400 is activated for a session, during which the treated area simultaneously receives electrical stimulation and thermal therapy. Of course, the TENS unit 400 and electrodes may be used without hydrating and/or freezing or heating the laminate 100. Likewise, the frozen or heated laminate 100 may be used without the TENS unit 400. However, used together, the thermal media and electrical stimulus are believed to provide a superior therapy session.

While an exemplary embodiment of the invention has been described, it should be apparent that modifications and variations thereto are possible, all of which fall within the true spirit and scope of the invention. With respect to the above description then, it is to be realized that the optimum relationships for the components and steps of the invention, including variations in order, form, content, function and manner of operation, are deemed readily apparent and obvious to one skilled in the art, and all equivalent relationships to those illustrated in the drawings and described in the specification are intended to be encompassed by the present invention. The above description and drawings are illustrative of modifications that can be made without departing from the present invention, the scope of which is to be limited only by the following claims. Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents are intended to fall within the scope of the invention as claimed.

What is claimed is:

1. A wearable nerve-stimulating thermal wrap comprising:
- a thermal media laminate comprised of a web of plastic film sealed at a plurality of locations to a web of fabric with spaces between the sealed locations comprising cells, each cell being a pocket surrounded by locations at which the plastic film is sealed to the web of fabric, each cell containing an absorbent solid state thermal medium, said thermal media laminate further comprising at least one electrode area, each electrode area being devoid of cells and being sized and shaped to receive a transcutaneous electrical nerve stimulation electrode,
- an insulating backing attached to the plastic film opposite the web of fabric,
- a transcutaneous electrical nerve stimulation electrode attached to at least one electrode area, a wire lead extending from the transcutaneous electrical nerve stimulation electrode,
- a first aperture in the thermal media laminate at one of the locations at which the plastic film is sealed to the web of fabric adjacent to one of the at least one electrode area, and a second aperture in the insulating backing in alignment with the first aperture, the wire lead of the transcutaneous electrical nerve stimulation electrode extending through the first aperture and the second aperture,
- an attachment band attached to the thermal media laminate, said attachment band being sized to releasably secure the thermal media laminate to a wearer, and
- a transcutaneous electrical nerve stimulation unit operably coupled to the wire lead of the transcutaneous electrical nerve stimulation electrode.

2. The wearable nerve-stimulating thermal wrap according to claim 1, the at least one electrode area comprising a fenestration in the thermal media laminate.

3. The wearable nerve-stimulating thermal wrap according to claim 1, the absorbent solid state thermal medium comprising a superabsorbent, multiply-cross-linked polymer.

* * * * *